United States Patent [19]

Goettsche et al.

[11] Patent Number: 4,461,721
[45] Date of Patent: Jul. 24, 1984

[54] WOOD PRESERVATIVE

[75] Inventors: Reimer Goettsche, Baden-Baden; Hans-Norbert Marx, Buehl-Weitenung, both of Fed. Rep. of Germany

[73] Assignee: BASF Aktiengesellschaft, Fed. Rep. of Germany

[21] Appl. No.: 367,588

[22] Filed: Apr. 12, 1982

[51] Int. Cl.³ ................................................ C09K 3/28
[52] U.S. Cl. ................................ 252/607; 106/18.13; 106/18.3; 252/400 R; 252/602; 427/440; 428/921
[58] Field of Search ................ 252/400.1, 602, 607; 427/317, 440; 428/921; 106/18.3; 8/196, 116 R

[56] References Cited

U.S. PATENT DOCUMENTS

| | | | |
|---|---|---|---|
| 3,874,990 | 4/1975 | Surdyk | 428/921 |
| 4,012,507 | 3/1977 | Knoepfler et al. | 428/921 |
| 4,071,645 | 1/1978 | Kahn | 428/500 |
| 4,076,540 | 2/1978 | Stossel | 252/2 |
| 4,076,871 | 2/1978 | Short et al. | 428/921 |
| 4,143,153 | 3/1979 | Pommer et al. | 424/289 |
| 4,145,296 | 3/1979 | Fox et al. | 252/2 |
| 4,184,969 | 1/1980 | Bhat | 428/921 |
| 4,269,626 | 5/1981 | Gorke et al. | 106/18.32 |

FOREIGN PATENT DOCUMENTS

| | | | |
|---|---|---|---|
| 2140051 | 7/1972 | Fed. Rep. of Germany . | |
| 3030242 | 3/1982 | Fed. Rep. of Germany . | |
| 55-34905 | 3/1980 | Japan | 427/440 |
| 55-30961 | 3/1980 | Japan | 427/440 |

OTHER PUBLICATIONS

Central Patent Index, Basic Abstracts Journal C, AGDOC, Week Y28, 1977, Nr. 49624y, Derwent Publications, London.

*Primary Examiner*—Benjamin R. Padgett
*Assistant Examiner*—Howard J. Locker
*Attorney, Agent, or Firm*—Keil & Weinkauf

[57] ABSTRACT

A wood preservative based on an aqueous mixture of boric acid and a water-soluble organic amine, which mixture additionally contains sodium polyborate or a mixture of boric acid and borax.

10 Claims, No Drawings

WOOD PRESERVATIVE

The present invention relates to an aqueous wood preservative based on boric acid and an organic amine.

It is known from German Pat. No. 2,140,051 that a concentrate having a high content of boric acid, for example a mixture (composite) of diethanolamine, boric acid and water, is useful as a wood preservative.

If alkanolamines are used as solvents for the boric acid, the concentrates are of limited use as flameproofing paints. The concentrates are strongly hygroscopic, and though they dry initially, the coating on the wood becomes very tacky after a period of time which varies depending on the atmospheric moisture and temperature. If other amines, for example polyamoines, are used, the material dries excessively on the wood, so that the coatings in due course become brittle and craze. If the compositions are employed, as aqueous solutions (usually containing 90-75% by weight of water), as wood preservatives, and are applied by brushing, spraying or dipping, the penetration of the boric acid into the wood is adversely affected by the insufficient penetration of the amine, which is instantly bonded to the surface of the wood.

We have found that a wood preservative comprising a boric acid/water-soluble organic amine composite, water and sodium polyborate or a mixture of boric acid and borax, does not show the disadvantages mentioned above. All or most of the composite may be in the form of the boric acid salt of the amine, but the composites need not contain stoichiometric equivalents and free amine etc. may be present. The wood preservative according to the invention can be used both to protect the wood against attack by fungi and insects and as a flameproofing agent for protecting the wood from being set alight by fire.

Examples of suitable water-soluble organic amines are primary, secondary or tertiary organic amines, as well as diamines, triamines, tetramines and pentamines, and hydroxy derivatives and methoxy derivatives of the said amines. Specific examples are monoethanolamine, diethanolamine, triethanolamine, monomethylethanolamine, methyldiethanolamine, ethylamine, diethylamine, propylamine, methoxyethylamine, methoxypropylamine, dimethylethanolamine, 1,2-propylenediamine, 3-amino-1-methylaminopropane, dipropylenetriamine, tripropylenetetramine, tetrapropylenepentamine and mixtures of these. Monoethanolamine is preferred.

In the case of most amines, it suffices to stir the boric acid into the amine. Since the resulting liquids may however be too viscous, it can be advisable to add a small amount of water when using the compositions. The concentrate is easily prepared above a pH of from about 6.5 to 7.5. Below this pH, dissolution of the boric acid in the amine or polyamine is more difficult. A pH of from about 7.5 to 8.0 corresponds to a ratio of about 1 mole of monoamine to 3-4 moles of boric acid. When using the polyamines, each amine radical of the polyamine molecule corresponds to about 3 moles of boric acid, i.e. for neutralization of 1 mole of triamine for example 9 moles of boric acid are required. Any higher pH can readily be obtained by increasing the proportion of amine or of polyamine.

Sodium polyborate ($Na_2B_8O_{13} \cdot 3H_2O$) is a solid, water-soluble compound which is formed on reaction of boric acid with borax in water. The wood preservative according to the invention can accordingly contain sodium polyborate or a mixture of boric acid and borax, since the latter, as mentioned above, is converted to sodium polyborate. In preparing the wood preservative according to the invention, it is preferred to add a mixture of boric acid and borax, or to add boric acid and borax alternately, to the aqueous composition obtained by mixing the water-soluble amine and boric acid.

The wood preservative according to the invention contains, for example, from 20 to 60 parts by weight of the boric acid/water-soluble organic amine composite. To this is added, for example, from 40 to 80 parts by weight of sodium polyborate or, preferably, of a mixture of boric acid and borax. The weight ratio of boric acid to borax in the mixture added is, for example, from 2:1 to 1:1.2, preferably 1:1.

The wood preservative according to the invention is, for example, a viscous wood preservative and flameproofing paste containing a total of 40% by weight of $B_2O_3$, and having a solubility of more than 25% in water at 20° C.

The paste is obtained, for example, by slowly stirring sodium polyborate, or boric acid/borax, into the boric acid/amine composite. In the latter case, whilst the material is being stirred in, reaction of boric acid and borax results in elimination of water and formation of sodium polyborate, which precipitates in a very fine crystalline form (1–10 $\mu$m) and then, together with the boric acid/amine composite, forms the paste.

The ratio of boric acid to borax in the composite of these two ingredients is chosen in accordance with the pH of the boric acid/amine composite, so that the wood preservative according to the invention and its aqueous solutions have a pH of from 6 to 8 at 20° c. A greater or lesser amount of water can be added, as required, to the wood preservative according to the invention, in order to obtain the desired viscosity.

The sedimenting characteristics, and/or the brushing properties, of the wood preservative can be improved by adding thickeners and thixotropic agents.

In the following Examples parts and percentages are by weight.

EXAMPLE 1

Boric acid/amine concentrate 1, consisting of 20 parts by weight of monoethanolamine, 60 parts of boric acid and 20 parts of water.

Wood preservative, consisting of 33 parts of boric acid/amine concentrate 1 and 67 parts of a 1:1 borax/boric acid mixture.

Preparation:

The boric acid/amine concentrate is introduced into a stirred vessel and boric acid and borax are added alternately, whilst stirring. Stirring is continued until the boric acid and borax crystals have dissolved and the sodium polyborate has formed and separated out.

Coatings of the wood preservative, applied in 2 passes, in a total amount of 300–450 g/m$^2$, to wood, dry very rapidly. They are not hygroscopic and do not become tacky or brittle, even after a lengthy period.

Application characteristics as a flameproofing agent:

Amount applied: 350 g/m$^2$; the wood is then stored at about 75% atmospheric humidity/20° C. for a period of 4 weeks.

The boric acid/amine concentrate gives very tacky coatings after drying.

The wood preservative according to Example 1 dries without crazing and is neither brittle nor tacky.

On exposure to heat, the wood preservative according to Example 1, present on the wood, forms a microscopic layer of boron trioxide foam, with elimination of water, and this layer serves as an insulating agent for the wood below it. The normally flammable wood acquires low flammability as a result of the coating. Penetrating capacity when used as a wood preservative:

Sample pieces of wood are brushed with 10% strength aqueous solutions and after 7 days the depth of penetration is determined by testing the wood with Kurkuma reagent.

The boric acid/amine concentrate is applied at the rate of 50 g of concentrate/m² and gives a mean penetration (fiber saturation) of 3.6 mm.

The wood preservative according to Example 1 is applied in an amount of 50 g/m² and gives a mean penetration of 6.2 mm.

EXAMPLE 2

Boric acid/amine concentrate 2: 15 parts of diethylenetriamine, 20 parts of water and 65 parts of boric acid.

Wood preservative consisting of: 50 parts of boric acid/amine concentrate 2 and 50 parts of a 1.2:1 mixture of boric acid/borax.

The method of preparation is as described in Example 1. Application characteristics as a flameproofing agent:

Amount applied: 350 g/m²; the wood is then stored at about 65% atmospheric humidity/20° C. for a period of 4 weeks.

Boric acid/amine concentrate 2: a dry crazed film is obtained.

Wood preservative according to Example 2: the film is dry, free from crazing, and neither brittle nor tacky. Penetrating capacity when used as a wood preservative:

Sample pieces of wood are brushed with 10% strength solutions and after 7 days the penetration is determined with Kurkuma reagent.

Boric acid/amine concentrate 2: mean penetration (fiber saturation) 3.2 mm.

Wood preservative according to Example 2: mean penetration 6.0 mm.

Colored coatings and colored wood preservative solutions can be prepared by adding pigment preparations or dyes. The addition of wetting agents assists instant wetting of the wood by the wood preservative.

We claim:

1. A wood preservative comprising an aqueous composition which consists essentially of:
   (a) from 20 to 60 parts by weight of a salt forming composite consisting of boric acid and a water-soluble organic amine, and
   (b) from 40 to 80 parts by weight of sodium polyborate or a mixture of boric acid and borax in a weight ratio of from 2:1 to 1:1.2 leaving out of account the boric acid present as the salt of the organic amine, and wherein said 40 to 80 parts by weight is determined by leaving out of account the presence of water and the boric acid present as the salt of the organic amine.

2. A wood preservative as claimed in claim 1 wherein the amine contains up to 8 carbon atoms, up to 5 amino nitrogen atoms and optionally one or more hydroxy or methoxy groups.

3. A wood preservative as claimed in claim 2, wherein the amine is monoethanolamine.

4. A process for preparing a wood preservative which comprises:
   (a) producing an amine salt forming concentrate by stirring boric acid into a water-soluble organic amine;
   (b) adding sodium polyborate or boric acid and borax in a weight ratio of 2:1 to 1:1.2 to said concentrate while stirring to form an admixture thereof; and
   (c) adding water to said admixture in the amount required to obtain the viscosity desired in the resulting wood preservative product.

5. A process as claimed in claim 2 wherein the boric acid is stirred into the amine at a pH of at least 6.5 to 7.5 in the presence of water.

6. A process as claimed in claim 2 or 5, wherein either a mixture of boric acid and borax is added or boric acid and borax are added alternately, so that sodium polyborate is formed in situ in the presence of water.

7. A process as claimed in claim 6, wherein the weight ratio of boric acid to borax is chosen so that the wood preservative or an aqueous solution thereof has a pH of from 6 to 8 at 20° C.

8. A process for protecting wood against fungal and insect attacks and fireproofing it comprising applying the wood preservative of claim 1 to the wood surface.

9. A process as claimed in claim 8 wherein the wood preservative is applied to the wood surface in an amount of from 300 to 450 g/m².

10. A process for protecting wood against fungal and insect attack and fireproofing the wood which comprises: applying the wood preservative described in claim 2 to the wood surface.

* * * * *